US009976120B2

(12) United States Patent
Blick et al.

(10) Patent No.: US 9,976,120 B2
(45) Date of Patent: May 22, 2018

(54) TUBULAR SCAFFOLD FOR NEURAL GROWTH

(75) Inventors: Robert H. Blick, Madison, WI (US); Justin Williams, Cambridge, WI (US); Minrui Yu, Madison, WI (US); Yu Huang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 767 days.

(21) Appl. No.: 12/880,776

(22) Filed: Sep. 13, 2010

(65) Prior Publication Data

US 2012/0064628 A1 Mar. 15, 2012

(51) Int. Cl.
*C12N 5/0793* (2010.01)
*C12M 1/12* (2006.01)
*H01L 27/00* (2006.01)

(52) U.S. Cl.
CPC .......... *C12N 5/0619* (2013.01); *C12M 25/14* (2013.01); *C12N 2535/00* (2013.01); *H01L 27/00* (2013.01)

(58) Field of Classification Search
CPC .... C12M 25/14; C12N 5/069; C12N 2535/00; A61B 5/04888; A61B 5/0031; A61B 5/4528
USPC ...................................... 435/399; 607/48, 60
See application file for complete search history.

(56) References Cited

U.S. PATENT DOCUMENTS

2008/0061798 A1* 3/2008 Blick ............................ 324/642
2008/0228240 A1* 9/2008 Edell et al. .................... 607/48
2008/0300663 A1 12/2008 Blick et al.

OTHER PUBLICATIONS

Ben Ari. 2002. Excitatory actrions of GABA during development: the nature of nurture. Nature Reviews Neuroscience, v3, p. 728-739.*
Voets et al. (2003). TRPs make sense. Journal of Membrane Biology, v192, p. 1-.*
Zeck et al. (2001). Noninvasive neuroelectronic interfacing with synaptically connected snail neurons immbolized on a semiconductor chip. PNAS, v98(18), p. 10457-10462.*
Zhang et al (2007). Electrically conductive biodegradable polymer composite for nerve regeneration: electrically-stimulated neurite outgrowth and axon regeneration. Artificial Organs, v31(1), p. 13-22.*
Brushart et al. (2002). Electrical stimulation promotes motoneuron regeneration without increasing its speed or conditioning the neuron. Journal of Neuroscience, v22(15), p. 6631-6638.*
Bourzac. (2014). Silicon Nitride Microtubes Direct Neuron Growth. 3 pages.*
Froeter et al. Toward Intelligent Synthetic Neural Circuits: Directing and Accelerating Neuron Cell Growth by Self-Rolled-Up Silicon Nitride Microtube Array. ACS Nano (2014), v8(11), p. 11.08-11117.*

(Continued)

*Primary Examiner* — Sean C. Barron
(74) *Attorney, Agent, or Firm* — Boyle Fredrickson S.C.

(57) ABSTRACT

A scaffold for neurons consists of tubes sized to promote neural growth through the tubes. The tubes may be fixed to a substrate providing electrical or optical paths out from the interior of the tubes from sensors or stimulating probes at one or more locations along the length of the coaxial axons. Steering electrodes at spaces between tubes may be used to selectively promote the growth of interconnections of different axons in a one, two, or three-dimensional fashion.

12 Claims, 4 Drawing Sheets

(56) References Cited

OTHER PUBLICATIONS

Smeal, Roy M., et al., The Influence of Substrate Curvature on Neurite Outgrowth Is Cell Type Dependent, pp. 281-292, Experimental Neurology 213 (2008), Elsevier, Inc., Burlington, MA, USA.
Schoen, Ingmar, et al., The Mechanism of Extracellular Stimulation of Nerve Cells on an Electrolyte-Oxide-Semiconductor Capacitor, pp. 1096-1111, Biophysical Journal, vol. 92, Feb. 2007, Biophysical Society, Rockville, MD, USA.
Schoen, Ingmar, et al., Extracellular Stimulation of Mammalian Neurons Through Repetitive Activation of Na+ Channels by Weak Capacitive Currents on a Silicon Chip, pp. 346-357, J Neurophysiol 100, 2007, The American Physiological Society, Bethesda, Maryland, USA.
Grant, P., et al., In Vitro Growth Properties of Xenopus Retinal Neurons Undergo Developmental Modulation, pp. 502-514, Developmental Biology 133, 1989, Academic Press, Inc., Elsevier, Inc., Burlington, MA, USA.

\* cited by examiner

TUBULAR SCAFFOLD FOR NEURAL GROWTH

STATEMENT REGARDING FEDERALLY SPONSORED RESEARCH OR DEVELOPMENT

This invention was made with United States government support awarded by the following agencies:
NSF 0520527
The United States government has certain rights to this invention.

BACKGROUND OF THE INVENTION

The present invention relates to a method and apparatus for the manipulation and investigation of cellular-level activity and in particular to a scaffold system for neurons permitting, in various embodiments, guided growth or interconnection of neurons and sensing or stimulation of neural activity.

The study of cellular activity, for example the operation of neurons, may require localized stimulation of individual or small clusters of cells. This may be done through the use of fine electrodes inserted into or near the cells and connected by leads to external equipment. The cells may be stabilized with the tip of a pipette or by using an on-chip cell measurement system such as is commercially available from Nanion Technologies associated with the domain of nanion.de or using a technology such as Neurochips offered by Infineon associated with the domain of infineon.com.

Particularly for neural tissues having complex interaction among neurons, such electrode systems can be difficult to place and can be impractical when multiple, closely spaced measurements need to be made.

SUMMARY OF THE INVENTION

The present invention provides a set of small tubes to which neurons can be attracted and which may in fact promote neurite through-growth. As constrained by such tubes, the growth and interconnection of neurons can be controlled and sensors and/or stimulating probes incorporated along the length of the tube used to provide precisely located but spatially separated measurements or stimulation.

In one embodiment of the invention, the invention provides a neural scaffold having a support structure and a plurality of tubes of biologically compatible material attached to the support structure and sized in diameter and length to permit the growth of axons therethrough.

It is thus a feature of at least one embodiment of the invention to provide a scaffold for guided growth and/or interconnection of neural tissue.

The tubes may have diameters in the range of one to 1000 μm and may have an aspect ratio length to diameter no less than 10.

It is thus a feature of at least one embodiment of the invention to provide tubes whose size and length may promote neural growth therethrough.

The tubes may be transparent to light or may be optically active.

It is thus a feature of at least one embodiment of the invention to permit visualization of the contained axon and possible optical stimulation of coaxially contained axons from an external source of light or from built-in optical components on the tube itself.

The tubes may comprise an outer and inner layer of different materials promoting curvature of the material of the tube into a cylinder by the relaxation of relative differences in strain between the different materials. In one embodiment the materials may be semiconductor materials, for example silicon and germanium or their alloys.

It is thus a feature of at least one embodiment of the invention to provide a simple method of precisely fabricating and locating tubes on a substrate using the power of conventional integrated circuit techniques applied to well-understood materials. This fabrication is readily adaptable to large scale patterns which may be used to produce large defined neural networks.

The tube may be closed sufficiently along its length to prevent exit of the axons exceptaxons except at ends of the tube.

It is thus a feature of at least one embodiment of the invention to channel axons along the length of the tubes for controlled interconnection. It is a further feature of this invention to provide an in vitro environment for studying neural processes that protect the neuron or axon from exposure to a culture solution such as may produce ion leakage through the cell membrane that affects the signal propagation and introduces signal noise The neural scaffold may further include an electrical conductor patterned on the inner surface of the tube and communicating from the tube to the support structure.

It is thus a feature of at least one embodiment of the invention to provide a simple method of sending or extracting signals to and from axons inside the tubes through traces extending to the substrate surfaces all of which may be fabricated using conventional integrated circuit fabrication techniques. It is another feature of at least one embodiment of the invention to permit establishment of electrical connections (including any one of ohmic, capacitive, or inductive connections) to large numbers of neurons.

The neural scaffold surface may be insulated by an insulator or passivated by biologically viable polymers, such as parylene layer over, but not limited to, the electrodes to provide for capacitive coupling to an axon in the tube.

It is thus a feature of at least one embodiment of the invention to eliminate the need for direct ohmic contact to the axons or the need for biocompatibility of the tube material or the conductor.

The neural scaffold may further include steering electrodes positioned near openings at ends of the tubes to guide a direction of neural growth in between tubes.

It is thus a feature of at least one embodiment of the invention to permit possible steering or switching of interconnections of neurons by electrical or electrically induced chemical stimuli.

The support structure may be planar (rigid or flexible) and may further include integrated circuitry on the support structure.

It is thus a feature of at least one embodiment of the invention to permit electrical decoding and/or processing circuitry to be incorporated into the scaffolding for management of multiple electrical signals associated with many neurons.

The tubes may be used with or without the substrate and may include multiple independent electrical probes spatially separated long a length of the tube affixed to the tube to provide electrical communication at different spatially separated points along a coaxially located axon.

It is thus a feature of at least one embodiment of the invention to provide for precise communication with an individual axon at multiple points, enabling sub-cellular detection or excitation along the path of signal propagation.

These particular objects and advantages may apply to only some embodiments falling within the claims and thus do not define the scope of the invention.

DETAILED DESCRIPTION OF THE PREFERRED EMBODIMENT

Figure 1:
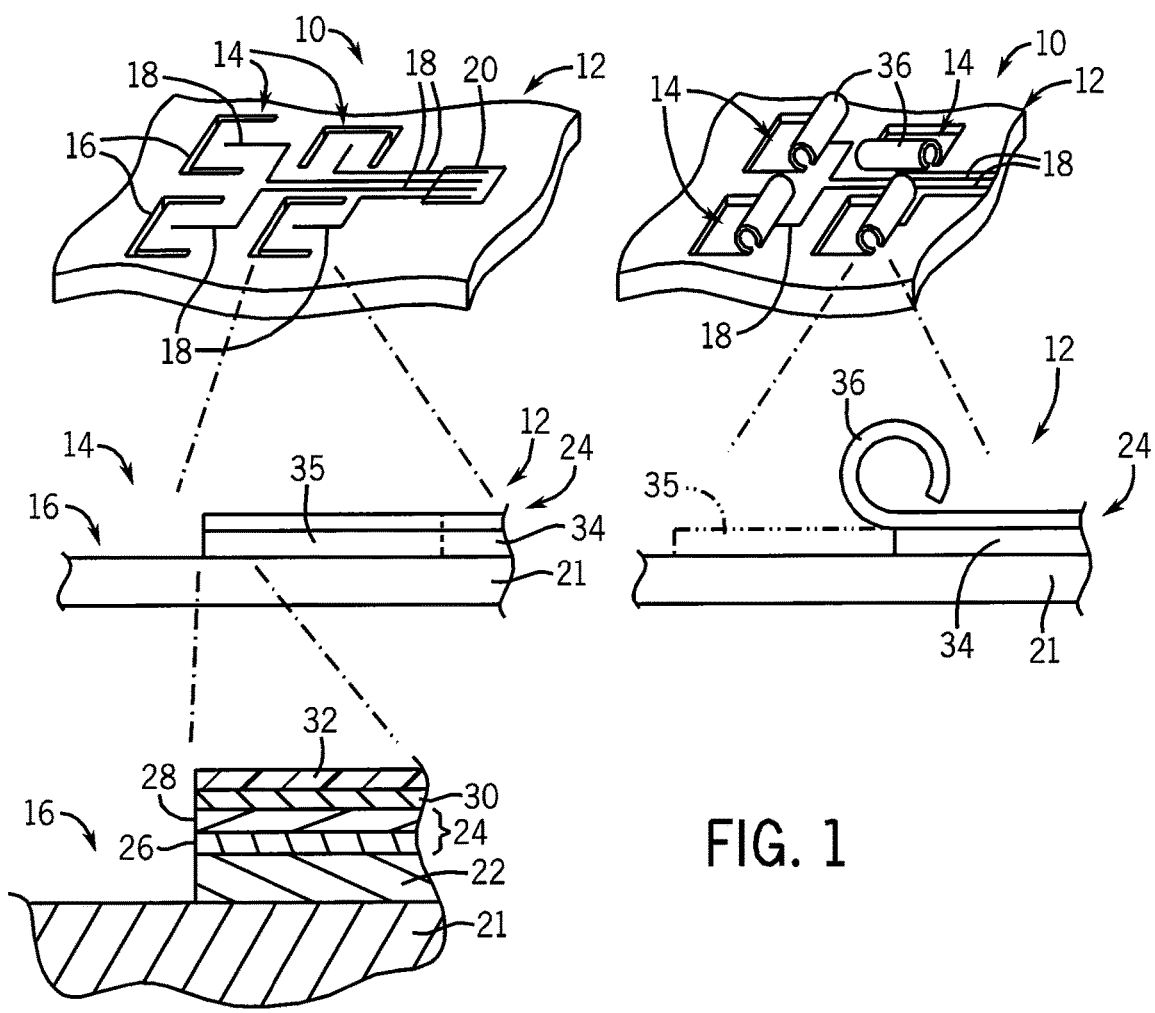
FIG. 1 is a fragmentary perspective view of a substrate at two stages of fabrication of substrate bound tubes, each first stage showing cross-sections of the substrate.

Referring now to FIG. 1, a neural scaffold 10 may provide for a support surface 12 having multiple pre-forms 14 etched therein providing, for example, C-shaped channels 16 describing three contiguous sides of a rectangle and having two opposed sides several millimeters in separation. Conductors 18 may be deposited or otherwise formed on an upper face of the support surface 12 within the boundaries of the channels 16 and extending outside of the channels (through the open side of the rectangle) to the support surface 12 outside of the pre-forms 14. Within the pre-forms 14, the conductors 18 may extend generally parallel to the opposed sides of the channels 16 by an amount substantially equal to the length of those opposed sides.

The conductors 18 may provide for electrical or optical conduction from the upper face of the support surface 12 between the pre-forms 14 to electrical circuitry 20 also formed on the support surface 12 using conventional integrated circuit techniques. Alternatively, the circuitry 20 may be placed on a separate integrated circuit and connected to the conductors 18, for example, by a jumper system, or the circuitry 20 may provide for other communications to off-site circuitry through serial data communication on conductors or near field or far field radio frequency links.

The support surface 12 may be formed from a substrate 21, for example a silicon wafer having on its upper surface a sacrificial layer 22, for example, composed of insulating silicon dioxide. A strained semiconductor bi-layer 24 may be formed on top of the sacrificial layer 22 comprising, for example, two successive layers of deposited semiconductor materials 26 and 28, materials 26 and 28 having lattice spacing that will produce an inherent strain in one or both layers. As will be discussed below, this inherent strain will cause the bi-layer 24 to curl when released from the sacrificial layer 22. The present tubes may be fabricated with diameters of about 10 nm to about 300 microns and wall thicknesses of about 100 nm to about 5 microns.

Suitable materials for bi-layer 24 include Si and SiGe as well as other semiconductor materials, for example, III/V-semiconductor materials. The bi-layer 24, for example, may be approximately 120 nm thick and extend over the entire surface of the support surface 12 except where removed in the channels 16. The production of such bi-layer 24 is taught, for example, in U.S. Pat. No. 7,229,901 entitled: "Fabrication of Strained Heterojunction Structures", U.S. patent application 2008/0061798 entitled: "Micro Coaxial Probes Made From Strained Semiconductor Bilayers" and U.S. patent application 2008/0300663 entitled: "Nano-And Micro-Scale Wireless Stimulating Probes", all assigned to the same assignee as the present invention and hereby incorporated by reference.

A conductor material 30 may be placed on top of the bi-layer 24 or infused or embedded within the bi-layer 24 to create conductors 18. For example, the material 30 may be a dopant or metallic applied to bi-layer 24 or a transparent material producing an optical waveguide. In some embodiments, a dielectric insulating layer 32 may be placed on top of the conductor material 30 and the bi-layer 24 to provide a surface that is biocompatible and electrically insulating. A suitable material is a layer of Parylene which may be applied by spin coating or other technique.

Referring still to FIG. 1, a portion 35 of the sacrificial layer 34 may be etched away undercutting the bi-layer 24 within the boundary of the channels 16, causing the bi-layer 24 in this region to roll into a tube 36 as a result of the geometry of the channels 16 and the strain between the materials 28 and 26. The length of the tube 36 is controlled by the separation of the opposed parallel walls of the channels 16 in the pre-forms 14 while the diameter is determined by the strain between the materials 28 and 26 such as may be controlled by selection of the lattice constant of those materials. Generally, these factors will be controlled to produce a diameter of the tube 36 in a range of one to 100μ and the length of several millimeters. This fabrication technique permits an unbroken conductor 18 to extend from an interior surface of the tube 36 and onto an upper surface of the support surface 12 to connect with other circuitry 20.

The formation of the above described structures may be performed by well-established integrated circuit processing techniques including etching, doping, metallization, planarization, and deposition all understood to those of ordinary skill in the art.

Figure 2:
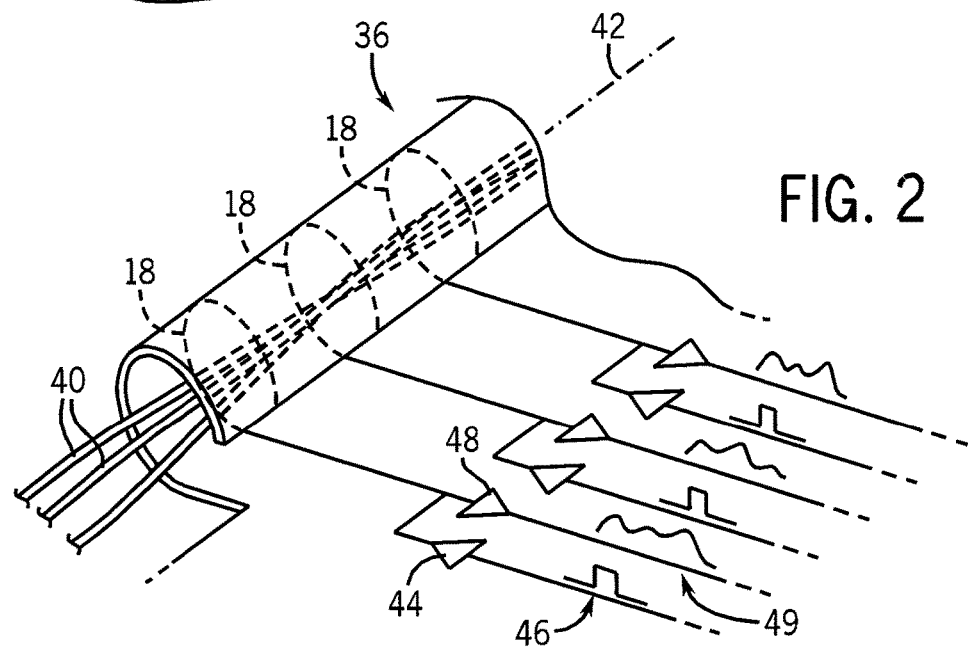
FIG. 2 is a schematic representation of multiple electrical connections to the interior of the tube for neural stimulation and/or sensing.

Referring now to FIG. 2, the inventors have determined that axons 40 may be encouraged to grow through the tubes 36 and that such growth, in fact, may be promoted by the dimensions of the tubes 36. Such axons growing through the tubes 36 will be coaxial with surrounding conductors 18 passing circumferentially along the inner diameter of the tube 36. Multiple conductors 18 may be spaced along the length of a given tube 36 separated along an axis 42 of the tube. Each conductor 18 may communicate with separate transmitting circuitry 44, for example instrumentation amplifiers forming part of circuitry 20 on the support surface 12 to receive, for example, pulse signals 46 that may stimulate the axons 40 at particular locations along the axon's length. Similarly, the conductors 18 may connect separate receiving circuitry, for example amplifiers 48, forming part of circuitry 20 that may receive neural signals 49 at the various locations along the tube 36 for communication to other parts of circuitry 20. The signals on each conductor 18 may be independently processed in parallel or through serial multiplexing.

As depicted in FIG. 2, generally the tube 36 may be at least partially open so long as the opening is small enough to constrain the axons 40 to within the tube 36 over all or a portion of its length. Alternatively, the walls of the tube 36 may overlap or wrap several times around themselves such as will still permit the necessary electrical communication to other portions of the substrate. This latter technique provides, in addition, another way to control wall thickness.

Figure 3:
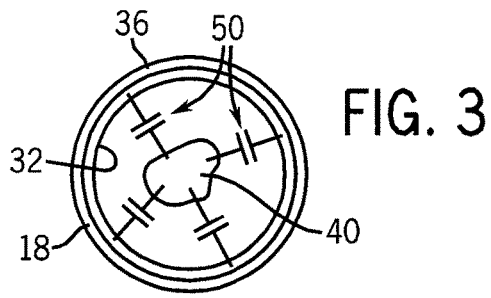
FIG. 3 is a cross-section through the tube of FIG. 2 depicting, schematically, an electrical connection provided by capacitive connection between an internal circumferential electrode and a coaxially contained axon.

Referring now to FIG. 3, the constrained axon 40 within the tube 36 may communicate with the conductors 18 through insulating layer 32 by means of capacitive coupling 50. Such capacitive coupling eliminates the need for the conductors 18 to directly contact the axon 40 allowing them to be made of materials that may not be biocompatible and further provides conduction to the axon 40 that may not be in direct contact with the conductor 18 for reasons of spacing within the tube 36.

Figure 4:
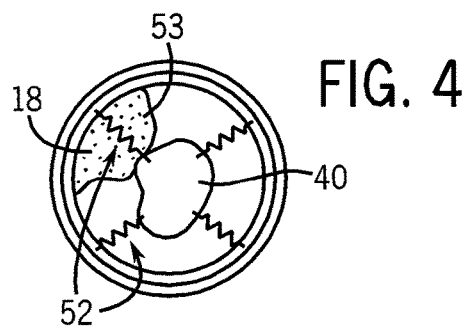
FIG. 4 is a figure similar to that of FIG. 3 showing an electrical connection provided by direct ohmic contact between the electrode and axon.

Referring to FIG. 4, alternatively a direct ohmic contact 52 may be established with an exposed conductor 18 that is biocompatible (for example gold or platinum) by omitting the insulating layer 32 possibly by an agency of an intervening electrolyte 53 such as a saline solution. It will be understood that the electrical connections possible with the present invention are not limited to capacitive or ohmic contact, but include inductive coupling (through small coils) and ionic diffusion.

Figure 5:
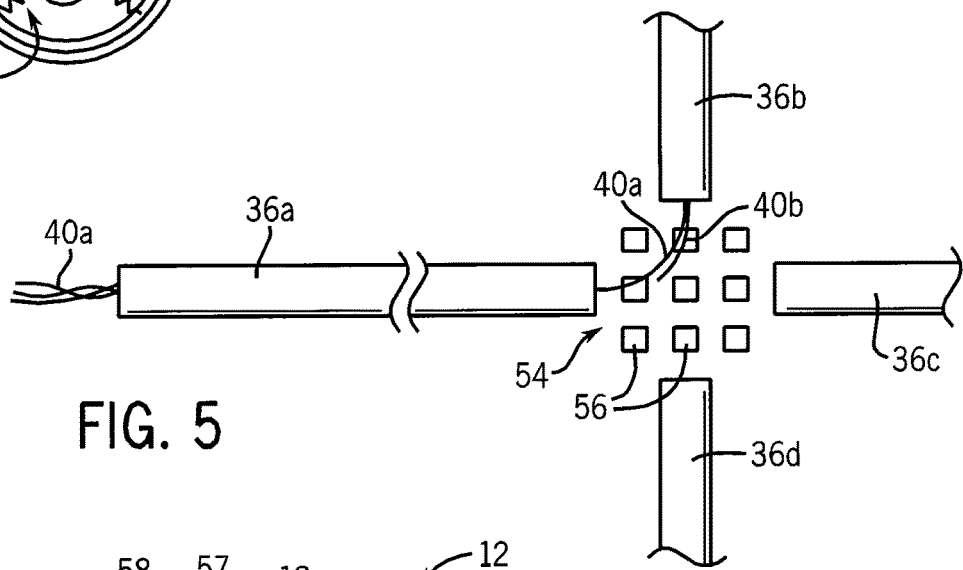
FIG. 5 is a top plan view of the substrate of FIG. 1 showing the placement of steering electrodes at the intersection between tubes, with the tubes placed in alignment on a regular rectilinear grid.

Referring now to FIG. 5, the present fabrication technique permits not only the formation of small tubes of predetermined diameter but also the precise location of those tubes on the support surface 12 by controls of the location of channels 16 (shown in FIG. 1). In one embodiment, the tubes 36 may be aligned with a regular rectilinear grid to provide periodic junction 54 at the perpendicular intersection of four tubes 36a-36d. A set of steering electrodes 56 may be in the area of the junction 54 bounded by the ends of the four tubes 36a-36d and be used to selectively steer neural growth, for example, promoting interconnection of a axon 40a in tube 36a with a axon 40b in tube 36b. Such steering may make use of an electrical field produced by the steering electrodes 56 or possibly electrically released chemicals on the electrodes 56. Electrodes 56 may be connected by surface conductors 18 similar to those used for the connection of the tubes 36 to circuitry 20.

The closed tube 36 may be sized to provide close contact with neurite surface over multiple dimensions much like the myeline sheath wrapping around the axon. In this respect the tube 36 may mimic the myelination of axons in vivo.

In an additional embodiment, microfluidic channels can be incorporated into the inner walls of the tube 36 to deliver growth factors or cells, such as Schwann cells, into the tubes 36. Schwann cells are understood to encourage regrowth of damaged axons, and may be attached to the inner surface of the tube, forming a real myelin layer in culture. This approach may be used to promote neuron outgrowth with real myelin and study axon repair.

Figure 6:
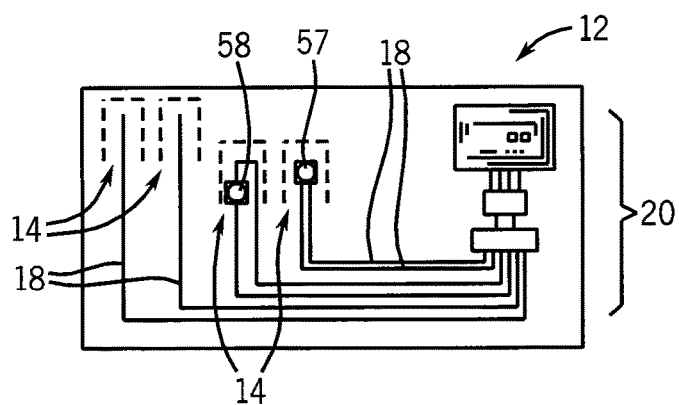
FIG. 6 is a planar view of the substrate of FIG. 1 before formation of the tubes showing placement of integrated circuit electronics, electrical conductors, photoelectric elements, and/or optical waveguides.

Referring now to FIG. 6, the present invention's formation of tubes by a rolling of a strained semiconductor bi-layer 24 permits simple processing of the support surface 12 in its planar form. This processing may be used not only to simply form and route the conductors 18, but also to permit the fabrication of semiconductor devices such as photoelectric devices 58 and 57 on the inner surface of the tubes 36 prior to the rolling. This fabrication may be conducted in parallel with the fabrication of the other circuitry 20 described above which may include, for example, computer processors, data acquisition circuitry, multiplexing circuitry, amplifier circuitry, and light emitting and light detecting circuitry. For example, photoelectric device 58 may be a photo diode and photoelectric device 57 may be a light emitting diode. Alternatively, the photoelectric devices 58 and 57 may be incorporated into the circuitry 20 and light conducted between the circuitry 20 and the photoelectric devices 58 and 57 in the tubes 36 by optical waveguides as described above. Alternatively, the materials of the bi-layer 24 may provide for an optically active junction between the layers made from III/V-semiconductor material to hence be optically active. This allows for emission of light from the tubes 36 directly into the cellular material. This light might be coherent (lasing), if desired.

Figure 7:
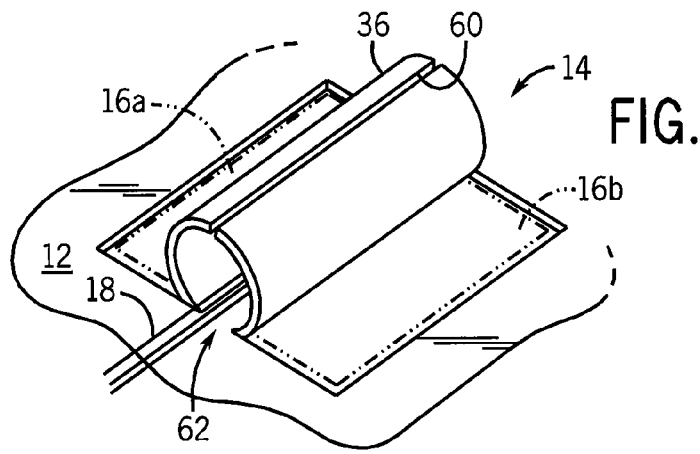
FIG. 7 is a perspective view of an alternative tube formation technique providing a seam at an upper edge of the tube and an axial conductor ingress.

Referring now to FIG. 7, in an alternative embodiment, each pre-form 14 may provide for two opposed C-shaped channels 16a and 16b whose bi-layers 24, when undercut, produce opposed cantilevered wings that curve upward to produce a tube 36 having a seam 60 (or overlap portion) along an upper edge of the tube 36 removed from the support surface 12. This tube 36 provides ingress for conductors 18 from the outer support surface 12 axially into the tube 36 at lower tangent points 62 at its open end where the tube 36 is attached to the support surface 12.

Figure 8:
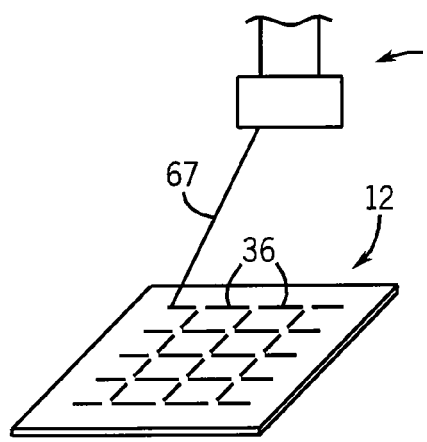
FIG. 8 is a simplified diagram of an optical stimulation device using a scanning laser for stimulation of axons contained in tubes.

Referring now to FIG. 8, axons within tubes 36 of the present invention may be alternatively stimulated with a scanning system 65 providing a steerable laser beam 67 for selectively irradiating particular ones of the tubes 36 to provide for selective direct activation of the axons contained therein by light energy, the release of photoactive chemicals, or the electrical activation of the axons by photoelectric elements 57 fabricated on inner walls of the tubes 36. The laser beam 67 may be steered to a particular tube 36 by a galvanic mirror assembly of the type well known in the art or similar scanning system.

Figure 9:
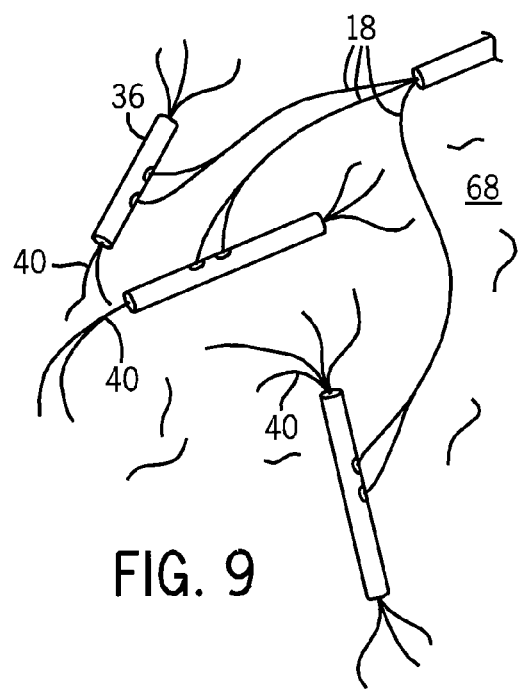
FIG. 9 is a representation of un-scaffolded tubes used for in vivo electrical communication with the brain or a neural mass.

Referring to FIG. 9, the tubes 36 may potentially be introduced into in vivo tissue 68 without a support surface 12, for example, by connecting the channels 16 into a closed rectangular periphery and wholly undercutting the bi-layer 24. Such floating tubes 36 may be tethered by individual conductors 18 or may communicate through wireless techniques, for example, as described in the above referenced patent application 2008/0300663. By communicating with coaxial axons 40, improved selectivity can be obtained as well communication with multiple spatially separated locations on an axon 40. The wireless communication may employ energy scavenging techniques such as those used with RFID technologies and may selectively respond to different frequencies or coded messages.

Figure 10:
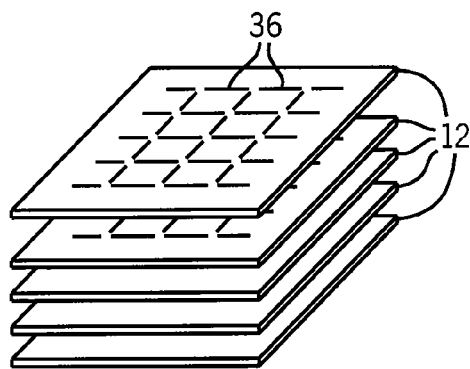
FIG. 10 is a simplified conceptual representation of the three-dimensional scaffolding system.

Referring now to FIG. 10, the ability to control and instrument axons in a two-dimensional surface can be extended to a three-dimensional volume, for example, by stacking multiple support surfaces 12 prepared as described above on top of each other. Connections of neurons between substrates may be controlled by selectively steering particular axons to regions of the support surface 12 that will match only with other desired interconnecting axons, for example by tubes 36 that do not lead to junctions with other tubes on the particular support surface 12. In this case, the support surfaces may be separated by spacers with interconnections provided by vias.

Generally, the conductors 18 described above may also be used to release deposited chemicals, for example by electrophoresis, sublimation, or electrochemical activity. Circuitry may be formed on the inner surface of the tubes 36 including antennas for receipt of energy or data or transmission of data, tuned circuits, logic circuits and the like. The tubes 36 may be constructed of piezoelectric materials allowing mechanical stimulation of the tubes 36 and/or the contained axons.

While the present invention describes the use of semiconductor and similar materials, the tubes 36 may be constructed of any biocompatible material including polymers that have been formed into tubes using differences in polymer swelling in solvents to provide the curving force rolling a bilayer into a tube. The present invention also contemplates that tubes may be formed by other known or yet to be developed microfabrication techniques. In addition the substrate 21, when used is not limited to silicon but may be other materials including flexible materials useful for example for implanted devices.

Figure 11:
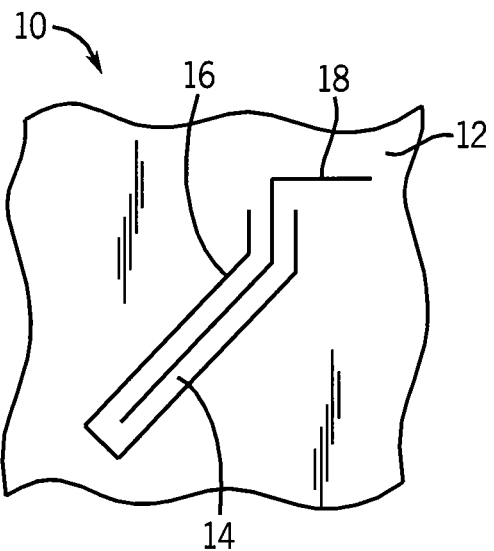
FIG. 11 is a top plan view of a support surface at a first stage of fabrication for providing a helical tube.
Figure 12:
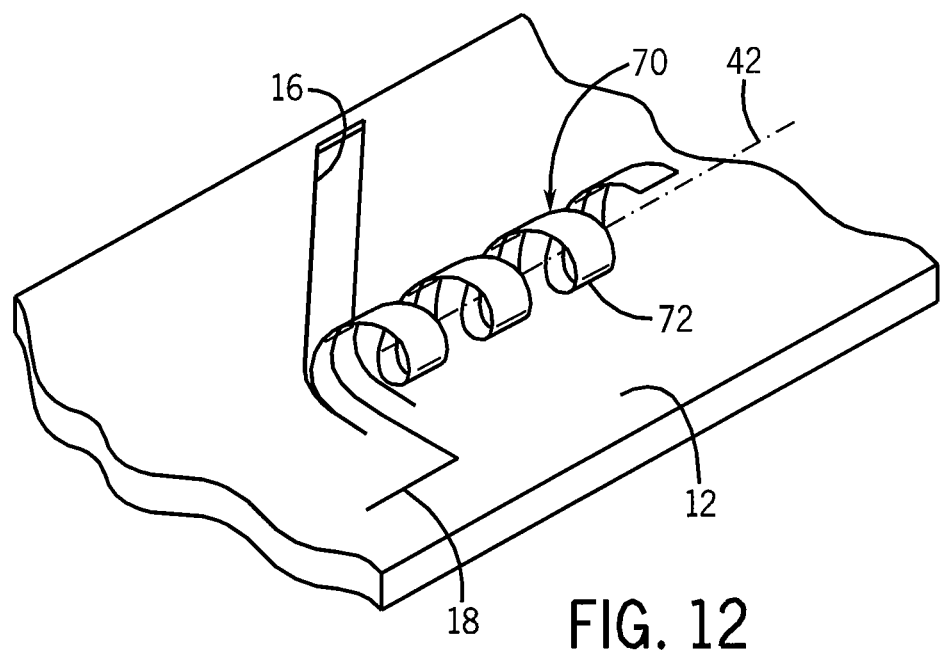
FIG. 12 is a perspective view of the support surface of FIG. 11 at the second stage of fabrication showing the generated helix.

Referring now to FIG. 11, in a variation on the above embodiments, the preform 14 may be adjusted in shape and orientation with respect to the strain axes so that when it is released, a loose helical spiral 70 is formed instead of the tube 36. The helical spiral 70 may be formed of a released narrow strip 72 which curls helically about axis 42 to conform to the outer surface of a cylinder aligned with that axis 42. The helical spiral 70 may have a pitch substantially equal to, but preferably larger than a width of the strip 72 so as to provide gaps between adjacent coils of the strip 72, the gaps following a similar helical path about axis 42. The cylinder defining the helical spiral 70 may, for example, have dimensions and can be arranged in a manner similar to the tubes 36 described above and may incorporate electrodes 18 and other electrical and optical elements described above and otherwise provide the features provided by the tubes 36 but for the helical form factor.

Such a helical tube 70 could be used to produce a neural scaffold comprising: a support structure; a plurality of helices of biologically compatible material attached to the support structure and sized in diameter and length to permit a growth of axons therethrough substantially constrained in direction along a length of the helix; whereby a pattern of neural growth can be controlled.

Generally, in a least one embodiment, the tubes or helix provide a three-dimensional contact to neural processes that may provide for stimulation and permit probing of the neural cell in a three-dimensional fashion over the neurite periphery. The tube wraps around the processes and insulates them from extracellular solution preventing passive ion leakage through the cell membrane like a myelin sheath. It is specifically intended that the present invention not be limited to the embodiments and illustrations contained herein and the claims should be understood to include modified forms of those embodiments, including portions of the embodiments and combinations of elements of different embodiments as come within the scope of the following claims. As used herein, the term "tube" should be understood broadly to be a passageway preventing egress of a axon except at the ends of the passageway and not limited to passageway is that our cylinders nor have straight axes. Tube should be considered to include conical as well as cylindericalcylindrical tubes, where the latter are made by using trapezoidal bilayers. When the term diameter is used to describe the tubes, it is not intended to limit the tubes to those with circular cross-sections, but should be broadly understood when applied to noncircular tubes to be the diameter of a circle of corresponding area to the cross-section of the tube. Generally, the invention contemplates that the neuron itself may but need not be fully or partially enclosed in the tube through which axons may be induced to grow.

We claim:

1. A method of providing an interface to neurons comprising the steps of:
    (a) providing a plurality of tubes free from tissue and/or bioactive molecules that segregate axons by function and sized in diameter and length to promote a growth of axons therethrough wherein the tubes are sized to wrap around neural processes of the neurons and insulate them from extracellular solution preventing passive ion leakage through a cell membrane of the neural processes as would be provided by a myelin sheath;
    (b) growing axons through the tubes as provided; and
    (c) providing at least one of a stimulating signal to the axon in the tube or a detection of signal from the axon constrained in the tube;
    further including the step of selectively interconnecting at least one axon growing through a first tube to a second axon growing through a second tube different from the first tube;
    wherein the tubes have diameters in a range of one to 100 μm and are sized to provide a three-dimensional contact to neural processes growing therethrough; and
    wherein the tubes have an aspect ratio of length to diameter no less than ten.

2. The method of claim 1 wherein the step of selectively interconnecting employs electrical stimulation.

3. The method of claim 1 wherein the tubes have a wall thickness with a range of substantially 100 nm to about 5 microns.

4. The method of claim 1 wherein the tubes are transparent to light.

5. The method of claim 1. wherein the tubes comprise an outer and inner layer of different materials and wherein the different materials are different semiconducting materials.

6. The method of claim 1 wherein the tube has an axial gap which is sufficiently closed along its length to prevent exit of the axon except at ends of the tube.

7. The method of claim 1 further including an electrical conductor patterned on an inner surface of the tube and communicating from the tube to a common support structure.

8. The method of claim 7 further including an insulating layer over the electrical conductor to provide for capacitive coupling to an axon in the tube.

9. The method of claim 1 further including steering electrodes positioned near openings at ends of the tubes to guide a direction of neural growth in between tubes.

10. The method of claim 1 wherein the tubes include integrated circuitry on walls of the tubes.

11. The method of claim 1 wherein the tubes are fixed to a substrate in a predetermined relative orientation.

12. The method of claim 1 wherein the tubes are fixed to a substrate in a predetermined relative orientation.

* * * * *